United States Patent
Hartranft et al.

[19]

[11] Patent Number: 6,139,754
[45] Date of Patent: Oct. 31, 2000

[54] HEMODIALYSIS CONDUCTIVITY SERVO-PROPORTIONING SYSTEM AND METHOD

[75] Inventors: Thomas J. Hartranft, Clearwater; Charles J. Dubauskas, St. Petersburg, both of Fla.

[73] Assignee: Baxter International Inc., Deerfield, Ill.

[21] Appl. No.: 07/795,908

[22] Filed: Nov. 15, 1991

[51] Int. Cl.[7] .......................... B01D 61/30; B01D 61/26; B01D 61/32

[52] U.S. Cl. .......................... 210/739; 210/85; 210/96.1; 210/101; 210/134; 210/143; 210/321.71; 210/646; 210/647; 210/742; 210/746

[58] Field of Search .......................... 210/85, 96.1, 101, 210/134, 143, 321.69, 321.71, 739, 742, 746, 645, 646, 647; 137/88, 98, 93; 422/62, 82.02, 105, 108

[56] References Cited

U.S. PATENT DOCUMENTS

| | | | |
|---|---|---|---|
| 3,847,809 | 11/1974 | Kopf | 210/321.71 |
| 3,992,301 | 11/1976 | Shippey et al. | 210/321.69 |
| 4,202,760 | 5/1980 | Storey et al. | 210/321.71 |
| 4,293,409 | 10/1981 | Riede et al. | 210/321.71 |
| 4,331,540 | 5/1982 | Witsoe | 210/321.69 |
| 4,399,036 | 8/1983 | Babb et al. | 210/321.71 |
| 4,508,622 | 4/1985 | Polaschegg et al. | 210/321.71 |
| 4,739,492 | 4/1988 | Cochran | 210/321.71 |
| 4,789,467 | 12/1988 | Lindsay et al. | 210/321.71 |
| 4,828,693 | 5/1989 | Lindsay et al. | 210/321.71 |
| 4,857,181 | 8/1989 | Shouldice et al. | 210/321.69 |
| 4,895,657 | 1/1990 | Polaschegg | 210/321.71 |
| 5,091,094 | 2/1992 | Veech | 210/647 |
| 5,094,748 | 3/1992 | Portillo, Jr. | 210/321.71 |

FOREIGN PATENT DOCUMENTS

| | | |
|---|---|---|
| 0 443 324 A1 | 8/1991 | European Pat. Off. . |
| 3223051 C2 | 12/1983 | Germany . |

OTHER PUBLICATIONS

Decision Revoking The European Patent (Article 102(1) EPC) European Patent No. 0567633 Mar. 25, 1999 Opposition Division: Germano A G Chairman Kempin H.—1st Examiner Peru L F J—2nd Examiner.

Dialysetechnik Herausgegeben von Dieter Schleipfer 4. übrarbeitete Auflage Bionic (1998).

Dialysis Technology Translation D2 4th Revised Edition Friedrichsdorf, 1988.

Blood Purification Process Technology and Clinical Science Translation D3 Goerg Thieme Verlag Stuttgart, New York, 1981.

*Primary Examiner*—John Kim
*Attorney, Agent, or Firm*—Paula J. F. Kelly; Charles R. Mattenson; Anibal Jose Cortina

[57] ABSTRACT

An improved conductivity based servo-proportioning system for hemodialysis machines. The servo-proportioning system calculates the actual conductivity contributions of the individual chemical components of the concentrate being utilized, to determine the conductivity set points. If an Acidified and Bicarb operation is being performed, then the servo-proportioning system calculates a conductivity set point at both an intermediate and final stage of the servo-proportioning system. If only acetate is being performed, then only the acetate individual chemical components are calculated. If the Na and/or Bicarb concentrations are to be varied, then the conductivity is calculated for the changed Na and/or Bicarb concentrations.

22 Claims, 2 Drawing Sheets

HEMODIALYSIS CONDUCTIVITY SERVO-PROPORTIONING SYSTEM AND METHOD

FIELD OF THE INVENTION

The present invention relates generally to controlling the dialysate concentrates of hemodialysis machines, and more particularly is directed to an improved conductivity based servo-proportioning system for hemodialysis machines.

BACKGROUND OF THE INVENTION

Hemodialysis machines are utilized by persons having insufficient or inoperative kidney functions. The machines may be used at a health facility or in the patient's home. The machine attaches to the patient through an extracorporeal circuit of blood tubing to a dialyzer having a pair of chambers separated by a thin semi-permeable membrane. The patient's blood is circulated through one of the chambers. The hemodialysis machine maintains a flow of a dialysate through the second chamber. Excess water from the blood is removed by ultrafiltration through the membrane and carried out by the dialysate to a drain.

A typical hemodialysis machine provides a pair of hoses which connect to the dialyzer and include a source of incoming water, a heat exchanger and heater for bringing the water to a required temperature, a source of dialysate concentrate or concentrates which are introduced into the water in a predetermined concentration and necessary pumps, pressure regulators, a deaerator, flow controllers and regulators. In an acetate dialysis system, only one concentrate is utilized, while in the more common bicarbonate dialysis systems, two concentrates, acidified and bicarbonate are utilized.

Bicarbonate dialysis is achieved by sequentially proportioning two concentrates and water into a single dialysate solution. The first mixture consists of water and the Acidified concentrate. For example, when performing Bicarbonate dialysis on a 36.83× concentrate basis, the Acidified concentrate contains different amounts of Sodium Chloride, Calcium Chloride, Magnesium Chloride, Potassium Chloride, Acetic Acid, and Dextrose. The nominal volumetric proportioning ratio is 34 parts of water to 1 part Acidified concentrate. The second mixture consists of the Water/Acidified result and the Bicarbonate concentrate. The Bicarbonate concentrate contains different amounts of Sodium Chloride and Sodium Bicarb. The nominal volume proportioning ratio is 19.13 parts Water/Acidified and 1 part Bicarbonate concentrate.

The Bicarbonate and Acidified concentrates are available in many different concentrations to allow a dialysate solution to be tailored for the individual patient. The concentrates are designated by the final concentrations of the chemicals based on the nominal proportioning ratios. In some cases it is desired that the final Sodium and/or Bicarbonate concentration differ from the nominal values. To obtain this, the volumetric mixing ratios are varied from the nominal values.

Acetate dialysis is achieved by the proportioning of a concentrate and water into a single dialysate solution. The nominal proportioning ratio is 34 parts of water to 1 part Acetate concentrate. The Acetate concentrate contains different amounts of Sodium Chloride, Calcium Chloride, Magnesium Chloride, Potassium Chloride, Sodium Acetate, and Dextrose.

The acetate concentrates also are available in many different concentrations again to allow a dialysate solution to be tailored for the individual patient. The concentrates are designated by the final concentrations of its chemicals based on the nominal proportioning ratios. In some cases it is desired that the final Sodium concentration differ from the nominal values. To obtain this, the volumetric mixing ratio is varied from the nominal values.

It is difficult to mix concentrates by volume accurately. This is even more difficult when the ratios are variable such as required in dialysis involving final concentrations that differ from the nominal concentrations. Servo-proportioning utilizing a feedback control based upon a classical proportional-integral control system was developed to achieve the desired concentrations.

Prior art systems, however, have been based upon nominal conductivity values. These nominal conductivity values have been attained from the concentration labels, which concentration values have been found to vary as much as plus or minus five (5) percent by Applicants. If the nominal Sodium (Na) or Bicarbonate (Bicarb) concentrate is to be varied, then the prior art systems again rely on nominal or estimated values, which again can produce errors in the actual final concentrations achieved.

SUMMARY OF THE INVENTION

The present invention is directed to an improved conductivity based servo-proportioning system for hemodialysis machines. The servo-proportioning system calculates the actual conductivity contributions of the individual chemical components of the concentrate being utilized, to determine the conductivity set points. If an Acidified and Bicarb operation is being performed, then the servo-proportioning system calculates a conductivity set point at both an intermediate and final stage of the servo-proportioning system. If only acetate is being performed, then only the acetate individual chemical components are calculated. If the Na and/or Bicarb concentrations are to be varied, then the conductivity is calculated for the changed Na and/or Bicarb concentrations.

These and other features and advantages of the invention will be more readily apparent upon reading the following description of a preferred exemplified embodiment of the invention and upon reference to the accompanying drawings wherein:

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE PREFERRED EMBODIMENTS

Figure 1:
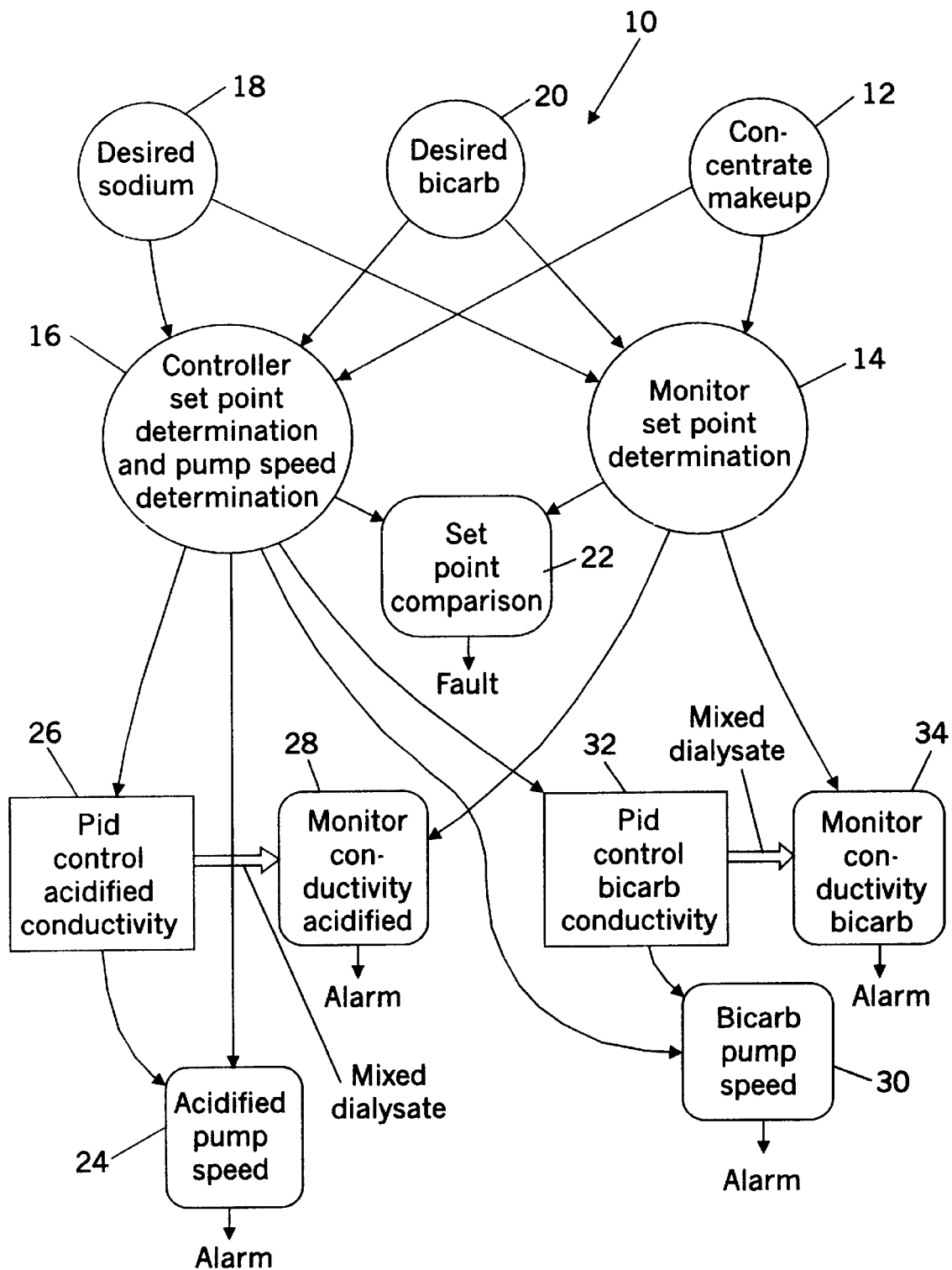
FIG. 1 is a schematic data flow diagram of one embodiment of the servo-proportioning system of the present invention.

Referring to FIG. 1, a flow diagram of the present invention is designated generally by the reference numeral 10. The nominal concentrate components indicated by a block 12, are first entered into a monitor 14 and also into a controller 16. The desired Na, indicated by a block 18, also is entered both into the monitor 14 and into the controller 16. The last component, presuming an Acidified/Bicarb operation, is the desired Bicarb indicated by a block 20 also is entered both into the monitor 14 and the controller 16.

The actual individual chemical component conductivity contributions are calculated and then a set point conductivity is calculated by both the monitor 14 and the controller 16. Their independent calculations are compared in a set point comparison block 22 and if they are not the same an error is generated. This provides a safety measure for the servo-proportioning system 10.

The controller 16 further determines the proper pump speeds to provide the proper proportioning ratio. The controller 16 drives the Acidified pump 24 with the pump speed controlled by a conductivity servo control loop 26. The pump drive, such as input pulses to a stepper motor, is adjusted according to a comparison of the sensed conductivity compared to the calculated conductivity set point. The monitor 14 monitors at 28 the conductivity of the Acidified dialysate and alarms if the conductivity is not within a set range of the conductivity set point. This provides control and monitoring at an intermediate or Acidified conductivity stage.

The servo-proportioning system 10 also controls and monitors the final calculated conductivity of Acidified and Bicarb by controlling a Bicarb pump speed 30 with a conductivity servo control loop 32. The controller 16 again senses the conductivity and drives the pump 30 to achieve the desired final set point conductivity. The final dialysate output of Acidified and Bicarb is again monitored by a block 34 and the monitor 14.

Figure 2:
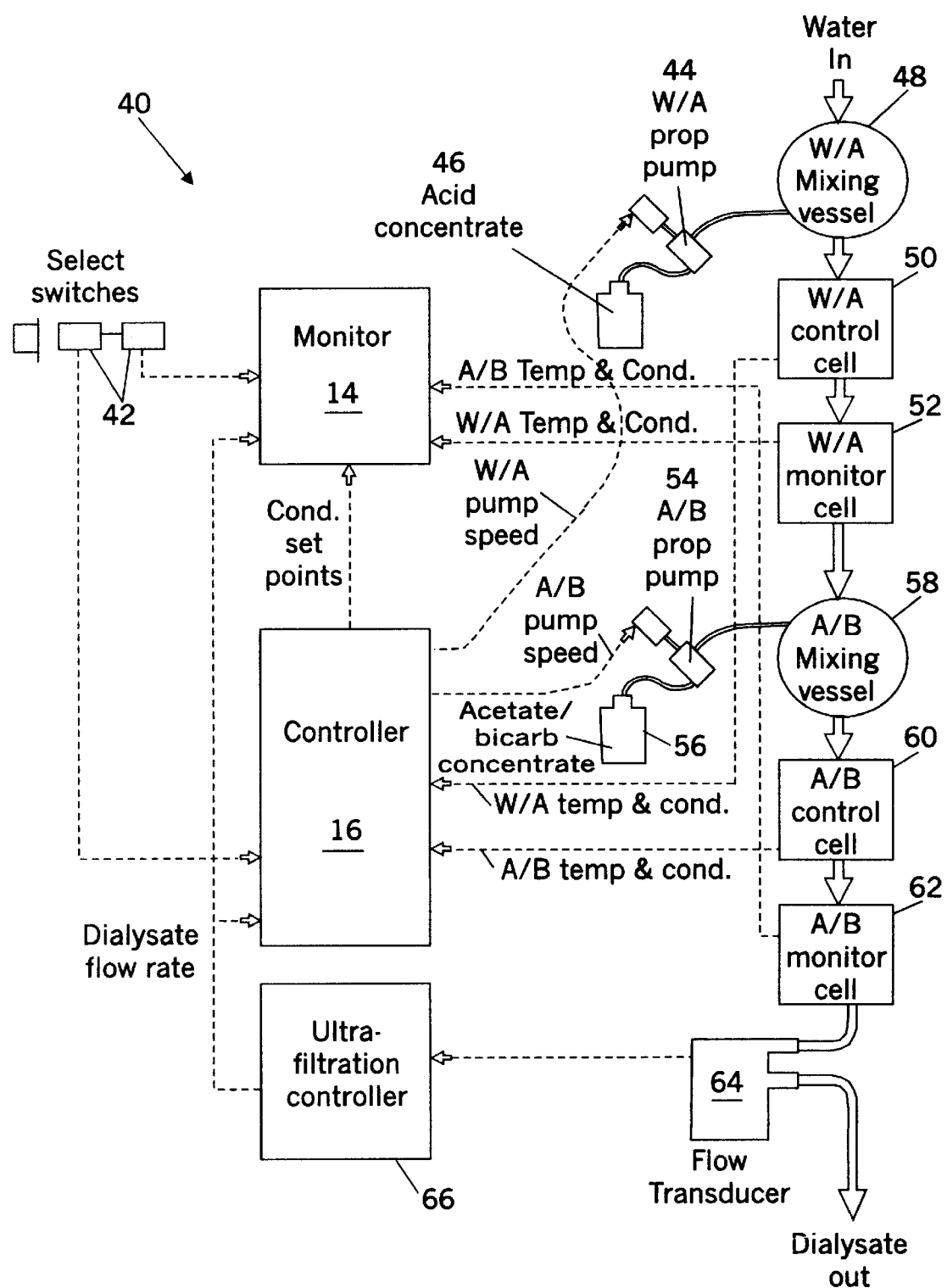
FIG. 2 is a schematic apparatus diagram of one embodiment of the servo-proportioning system of FIG. 1.

One embodiment of a servo-proportioning system apparatus for performing the dialysate operation of the present invention is designated by the reference numeral 40 in FIG. 2.

The components of the Acidified concentrate and the Bicarb concentrate are entered into the system 40 via a plurality of select switches 42 or in any other desired manner. This data is obtained from the concentrate manufacturer's label. For example purposes, each step of the operation is followed by an actual Bicarb example.

| | | |
|---|---|---|
| NaBicarb | 65.95059 | gm/l |
| NaCl | 23.52794 | gm/l |
| Na | 140 | meq/l |
| Cl | 108.5 | meq/l |
| Ca | 3.5 | meq/l |
| Mg | 1 | meq/l |
| K | 3 | meq/l |
| Acetate | 4 | meq/l |
| Bicarb | 35 | meq/l |
| Dextrose | 200 | mg/dl |

These concentrate components are expressed in terms of the final nominal diluted concentrations and thus must be converted to the actual concentrations of the concentrate components.

| BICARB CONCENTRATE | | |
|---|---|---|
| Bicarb | 785.07 | meq/l |
| Cl | 402.6 | meq/l |
| Na | 1187.67 | meq/l |
| ACIDIFIED CONCENTRATE | | |
| Na | 2983.23 | meq/l |
| Cl | 3259.455 | meq/l |
| Ca | 128.905 | meq/l |
| Mg | 36.83 | meq/l |
| K | 110.49 | meq/l |
| Acetic | 147.32 | meq/l |
| Dextrose | 7366 | mg/dl |

The desired final Na and desired final Bicarb, as defined by the operator, then are entered into the system 40. The final Bicarb initially produced will be reduced due to a chemical reaction with Acetic Acid.

| | |
|---|---|
| Na Offset | 10 meq/l |
| Bicarb | 25 meq/l |

The mixing ratio of the Acidified concentrate and the mixing ratio of the Bicarb concentrate are calculated to obtain the desired final Na and desired final Bicarb, as defined by the operator. The mixing ratio is the number of parts of incoming solution to be added to one part of concentrate.

| | |
|---|---|
| Water and Acidified | 26.48232 |
| Water/Acidified and Bicarb | 25.0348 |

Based upon the mixing ratios, proportioning pump stroke volume and the dialysate flow rate, the nominal proportioning pump speeds are calculated by the system 40.

Utilizing the mixing ratios and the concentrate component concentrations, the actual concentration of each component is calculated for the intermediate solution:

| | | |
|---|---|---|
| Na | 108.5509 | meq/l |
| Cl | 118.6019 | meq/l |
| Ca | 4.690471 | meq/l |
| Mg | 1.340135 | meq/l |
| K | 4.020404 | meq/l |
| Acetic | 5.360538 | meq/l |
| Dextrose | 268.02690 | mg/dl |

The actual concentration of each component also is calculated for the final solution.

| | | |
|---|---|---|
| Na | 150 | meq/l |
| Cl | 129.5103 | meq/l |
| Ca | 4.510309 | meq/l |
| Mg | 1.28866 | meq/l |

-continued

| | | |
|---|---:|---|
| K | 3.865979 | meq/l |
| Acetate | 5.154639 | meq/l |
| Bicarb | 25 | meq/l |
| Dextrose | 257.732 | mg/dl |

The conductivity contribution of each ionic concentrate component is calculated utilizing actual concentrations and equivalent conductivities corrected for the total ionic concentration.

| INTERMEDIATE | | |
|---|---:|---|
| Cl | 12487.42 | mmS/cm |
| Ca | 34.00888 | mmS/cm |
| Mg | 2.531359 | mmS/cm |
| K | 88.32753 | mmS/cm |
| Acetic | 64.59765 | mmS/cm |
| FINAL | | |
| Cl | 12936.09 | mmS/cm |
| Ca | 37.62258 | mmS/cm |
| Mg | 2.466231 | mmS/cm |
| K | 85.4439 | mmS/cm |
| Acetate | 438.3863 | mmS/cm |
| Bicarb | 2282.283 | mmS/cm |

The individual conductivity contributions then are summed to provide an intermediate conductivity set point of 12.65888 mS/cm and a final conductivity set point of 15.78249 mS/cm. The conductivity set points then are modified based upon the amount of dextrose present to provide an intermediate conductivity set point of 12.57018 mS/cm and a final conductivity set point of 15.74535 mS/cm.

In operation, the controller 16 drives a W/A pump 44, which meters an Acidified concentrate from a source 46 into a W/A mixing vessel 48. The Acidified concentrate is proportioned with water also input to the vessel 48. The dialysate then is sensed by the controller 16 via a W/A control cell 50 which provides a reading of the intermediate dialysate conductivity and temperature to the controller 16. The temperature is important because the conductivities typically are normalized to 25° C. The system 40 is set to operate in a range of about 34 to 39° C. and a one (1) degree change in temperature equates to about a 1.5 percent change in dialysate conductivity, so the readings must be temperature compensated.

The cell 50, the pump 44 and the controller 16 form a first servo-loop and the controller 16 adjusts the pump speed to achieve the correct intermediate dialysate conductivity. The dialysate conductivity also is monitored by the monitor 14 via a cell 52. The monitor 14 also compares the measured conductivity to a conductivity range set around the calculated conductivity set point. If the conductivity is out of the range the system 40 will alarm. The range can be, for example, plus and minus five (5) percent of the set point.

The controller 16 also controls a second Acetate/Bicarb pump 54, which meters a Bicarb concentrate from a source 56 into an A/B mixing vessel 58. The Bicarb is combined with the dialysate from the vessel 48 and the final dialysate then also is sensed by the controller 16 via an A/B control cell 60. The controller 16, with the pump 54 and the cell 60 again form a servo-control loop to achieve the desired final dialysate conductivity.

The final dialysate is monitored by the monitor 14 via monitor cell 62, to again provide an alarm if the final dialysate conductivity is out of range.

The monitor 14 and the controller 16 also are provided a final dialysate flow rate from a flow transducer 64 and an ultrafiltration controller 66, which provides a flow rate signal to the monitor 14 and the controller 16. The dialysate flow rate is very important, because the speeds of the pumps 44 and 54 are unique for each flow rate and are dependent upon the proportioning ratio.

The conductivity calculations are made independently by the monitor 14 and the controller 16. The pumps 44 and 54 also are driven independently of one another. The independent calculations and driving of the pumps 44 and 54 provides an added safety margin to the system 40 and also can be considered first and second stages of the system 40.

The pumps 44 and 54 preferably are the type of pumps disclosed in copending U.S. Ser. No. 07/685,584, filed Apr. 15, 1991, entitled Proportioning Device, which is incorporated herein by reference. The system 40 can be chemically treated as described in copending application docket number DI-4198, entitled automated hemodialysis chemical treatment system, filed concurrently herewith on Nov. 15, 1991, now U.S. Ser. No. 795,909, U.S. Pat. No. 5,244,568, which also is incorporated herein by reference.

We claim as our invention:

1. A method of mixing dialysate in a hemodialysis machine, comprising:

obtaining the nominal concentration values of individual concentrate components to be mixed as a dialysate;

entering the obtained nominal concentration values of the individual concentrate components into a monitor and into a controller;

calculating actual chemical component conductivity contributions from said obtained nominal concentration values separately with the monitor and with the controller;

calculating a set point conductivity of dialysate respectively from said calculated actual chemical component conductivity contributions, with both the monitor and with the controller;

comparing the set point conductivity calculated by the monitor with the set point conductivity calculated by the controller, and generating an error signal if they are not the same;

if set points are the same, determining a proper pump speed for at least one pump used to pump the concentrate components, to provide the proper proportioning ratio for the concentrate components, to result in a dialysate with a conductivity which matches the calculated set point conductivity, and driving the at least one pump for the concentrate components with the controller at the determined proper pump speed to mix the components to result in the dialysate;

sensing the conductivity of the resultant dialysate, and comparing it to the calculated conductivity set point, and if the sensed conductivity does not match the calculated conductivity set point, adjusting the operation of the at least one pump with the controller to thereby result in a sensed dialysate conductivity which matches the calculated conductivity set point.

2. The method as defined in claim 1 including defining an allowed conductivity range around said calculated set point dialysate conductivity and separately monitoring said dialysate conductivity and alarming if said monitored dialysate conductivity is outside of said range.

3. The method as defined in claim 1 including sensing the temperature of said dialysate and compensating said sensed dialysate conductivity for said sensed temperature.

4. The method as defined in claim 1 including performing a Bicarbonate dialysis operation and calculating an intermediate set point dialysate conductivity and a final set point dialysate conductivity.

5. The method as defined in claim 4 including sensing the intermediate conductivity of said dialysate and comparing said sensed intermediate dialysate conductivity with said calculated intermediate set point dialysate conductivity and controlling the proportion of said concentrate components and water in a first stage in accordance with said comparison to obtain a dialysate having a conductivity which is at the calculated intermediate set point dialysate conductivity.

6. The method as defined in claim 5 including sensing the final conductivity of said dialysate and comparing said final sensed dialysate conductivity with said calculated final set point dialysate conductivity and controlling the proportion of said concentrate components in a second stage in accordance with said comparison to obtain a dialysate having a conductivity which is at the calculated final set point dialysate conductivity.

7. The method as defined in claim 6 including defining an allowed conductivity range around said final set point dialysate conductivity and separately monitoring the dialysate conductivity throughout said method, and alarming if said monitored conductivity in outside of said range.

8. The method as defined in claim 6 including sensing the temperature of said dialysate in said second stage and compensating said sensed final conductivity for said sensed temperature.

9. The method as defined in claim 5 including sensing the temperature of said dialysate in said first stage and compensating said sensed intermediate conductivity for said sensed temperature.

10. The method as defined in claim 5 including defining an allowed conductivity range around said calculated intermediate set point dialysate conductivity and separately monitoring said dialysate conductivity and alarming if said monitored conductivity is outside of said range.

11. The method as defined in claim 1 wherein:
said sensing of the conductivity of the dialysate and adjusting the operation of each pump is conducted to result in an intermediate dialysate; and
further comprising, calculating a final dialysate conductivity set point with the controller and with the monitor, driving the least one pump at the pro per pump speed to mix the components to result in the final dialysate, sensing the conductivity of the final dialysate, and if the sensed conductivity does not match the calculated final dialysate conductivity set point, adjusting the operation of each pump with the controller to thereby result in a sensed final dialysate conductivity which matches the calculated final dialysate conductivity set point.

12. An apparatus for mixing dialysate in a hemodialysis machine, comprising:
a controller for having the nominal concentration value of individual concentrate components to be mixed to form dialysate input thereinto, said controller adapted for calculating a set point conductivity of dialysate from said nominal concentration values of individual concentrate components to be mixed to form the dialysate;
a monitor for having said nominal concentration values of individual concentrate components to be mixed to form a dialysate also input thereinto, and said monitor adapted for calculating a set point conductivity of dialysate from said nominal concentration values of individual concentrate components to be mixed to form the dialysate;
a comparison block for comparing the set point conductivity calculated by the controller with the set point conductivity calculated by the monitor, and adapted for generating an error signal if the calculated set point conductivities do not match;
pumps for pumping said individual concentrate components to be mixed to form said dialysate, said pumps connected to the controller to be driven thereby at a determined proper pump speed for the respective pump;
the controller further adapted for determining the proper pump speeds for the pumps which pump the individual concentrate components to be mixed, to result in a dialysate having a conductivity which matches the calculated set point conductivity, and for driving each pump at the determined pump speed;
a sensor connected for sensing the conductivity of the resultant dialysate, and the monitor connected to the sensor for receiving a signal representing the value of the sensed conductivity and comparing the sensed value to the calculated set point conductivity, for having the controller adjust the operation of the pumps according to the comparison of the sensed conductivity to the calculated conductivity set point to thereby result in a sensed dialysate conductivity which matches the calculated conductivity set point.

13. The apparatus as defined in claim 12 including means for defining an allowed conductivity range around said calculated set point conductivity, means for separately monitoring said dialysate conductivity and means for alarming if said monitored conductivity is outside of said range.

14. The apparatus as defined in claim 12 including means for sensing the temperature of said dialysate and means for compensating said sensed conductivity for said sensed temperature.

15. The apparatus as defined in claim 12, wherein said monitor is adapted for comparing the sensed conductivity of an intermediate dialysate with a calculated intermediate conductivity set point for having the controller drive the pumps to achieve an intermediate dialysate conductivity which matches the calculated intermediate dialysate conductivity set point; and said monitor further adapted for comparing the sensed conductivity of a final dialysate with a calculated final conductivity set point for having the controller drive each pump to achieve a final dialysate conductivity which matches the calculated final conductivity set point.

16. The apparatus defined in claim 15 including means for performing a Bicarbonate dialysis operation and means for calculating an intermediate set point dialysate conductivity and for calculating a final set point dialysate conductivity.

17. The apparatus as defined in claim 16 including means for sensing an intermediate conductivity of said dialysate, means for comparing said sensed intermediate dialysate conductivity with said calculated intermediate set point dialysate conductivity, and means for controlling the proportions of said concentrate components and water in a first stage in accordance with said comparison to obtain a dialysate having a conductivity which is the calculated intermediate set point conductivity.

18. The apparatus as defined in claim 17 including means for sensing the final conductivity of said dialysate, means for comparing said final sensed dialysate conductivity with said calculated final set point dialysate conductivity, and means for controlling the proportion of said concentrate components in a second stage in accordance with said comparison to obtain a dialysate having a conductivity which is at the calculated final set point dialysate conductivity.

19. The apparatus as defined in claim 18 including means for defining an allowed conductivity range around said calculated final set point dialysate conductivity, means for separately monitoring said final dialysate conductivity at any time and means for alarming if said monitored final dialysate conductivity is outside of said range.

20. The apparatus as defined in claim 18 including means for sensing the temperature of said dialysate in said second stage and means for compensating said sensed final dialysate conductivity for said sensed temperature.

21. The apparatus as defined in claim 17 including means for sensing the temperature of said dialysate in said first stage and means for compensating said sensed intermediate dialysate conductivity for said sensed temperature.

22. The apparatus as defined in claim 17 including means for defining an allowed conductivity range around said calculated intermediate set point dialysate conductivity, means for separately monitoring said intermediate dialysate conductivity at any time, and means for alarming if said monitored intermediate dialysate conductivity is outside of said range.

* * * * *